US00PP12379P2

(12) United States Plant Patent
Schusler

(10) Patent No.: US PP12,379 P2
(45) Date of Patent: Jan. 29, 2002

(54) DATURA PLANT NAMED 'REVEREND SCHUSLER'

(76) Inventor: Mark Joseph Schusler, 3200 Cr Ne 0092, Corsicana, TX (US) 75110-9432

( * ) Notice: Subject to any disclaimer, the term of this patent is extended or adjusted under 35 U.S.C. 154(b) by 0 days.

(21) Appl. No.: 09/395,307

(22) Filed: Sep. 13, 1999

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Annette H. Para

(57) ABSTRACT

A new cultivar of Datura plant named 'Reverend Schusler' characterized and distinguished from other Daturas by its uniquely colored foliage consisting of creamy yellow, yellow-white, grey-green and dark green patches with purplish coloration on the underside of the new growth (during cooler weather), the variegation extending to the sepals of the flowers, and the ovary, resulting in the fruit being white, yellow and green variegated; foliage and fruit being borne on purplish, tomentose stems, the sweetly fragrant flowers being a light lavender in color when young turning white as they mature.

9 Drawing Sheets

BACKGROUNG OF THE INVENTION (1) The present invention relates to a new and distinctive cultivar of Datura plant, also commonly known as Sacred Datura and Moon Flower, botanically known as *Datura wrightii* Regel, and known by the cultivar name 'Reverend Schusler'. The unusual coloration and variegation of this plant increases the aesthetic value of the plant for use in containers and to provide seasonal color in the landscape.

(2) *Datura wrightii* 'Reverend Schusler' was found by me in a planting of Datura seedlings in my garden located just east of Corsicana, Tex. and occurred as a sport(mutation) of one of those seedlings. The parent plant had foliage that was dark green to gray-green while the mutated branch had variegated foliage. Later it was found that the flower buds, calyxes, and fruit were also variegated.

Cuttings were taken off this plant and rooted under mist. Asexual propagation of 'Reverend Schusler' by tip cuttings has shown that the variegation is stable and succeeding generations of cuttings taken from both the original parent plant and rooted cuttings have developed offspring with similar variegation patterns, flower and fruit characteristics.

BRIEF SUMMARY OF THE INVENTION

A new and distinct cultivar of Datura plant characterized by its unusually white, yellow, and various shades of green colored variegated foliage, variegated calyxes on the flowers, and variegated fruit.

DETAILED BOTANICAL DESCRIPTION OF THE NEW PLANT VARIETY

Figure 1:
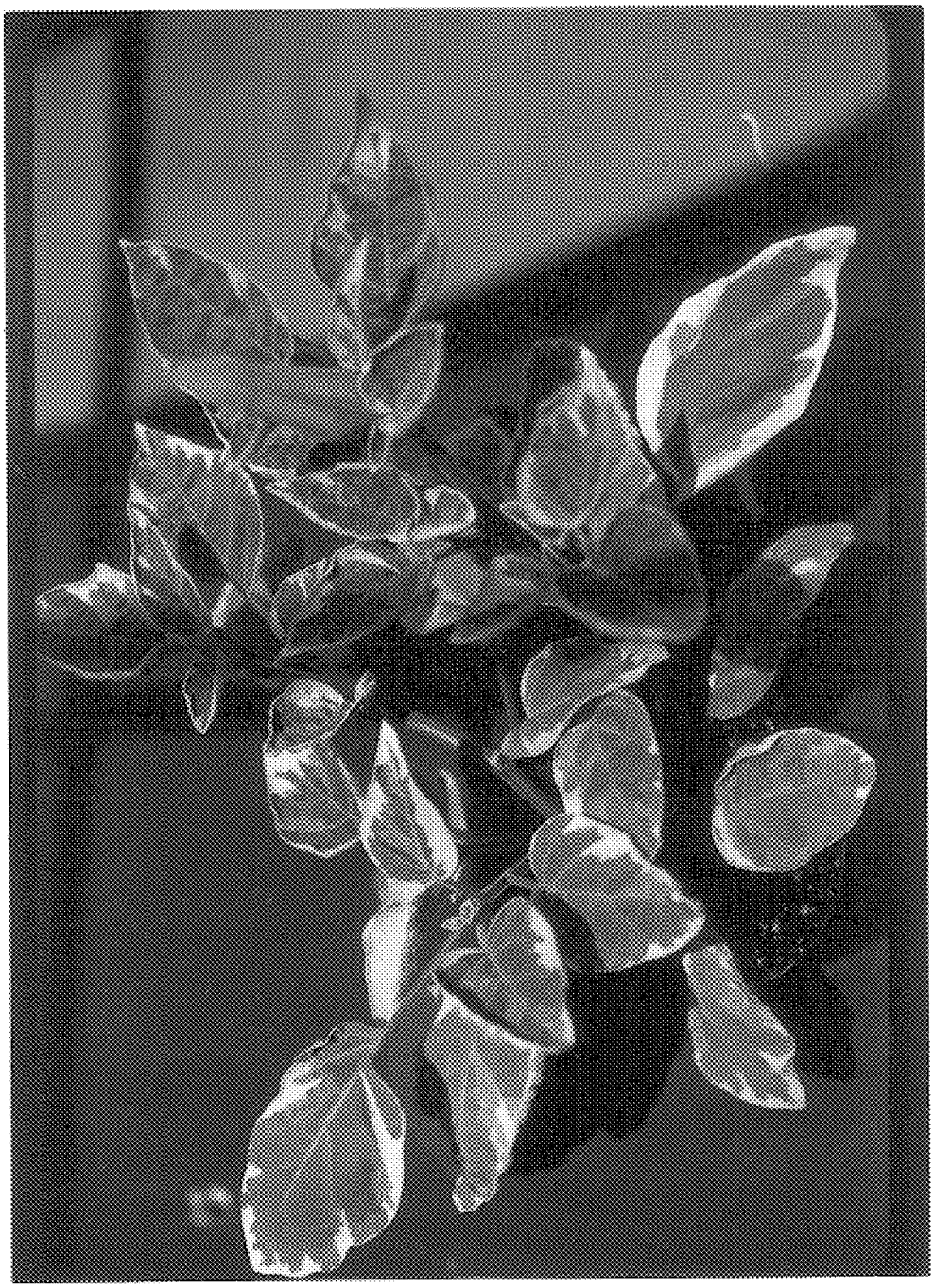
FIG. 1 Photograph of young plant with flower bud.
Figure 2:
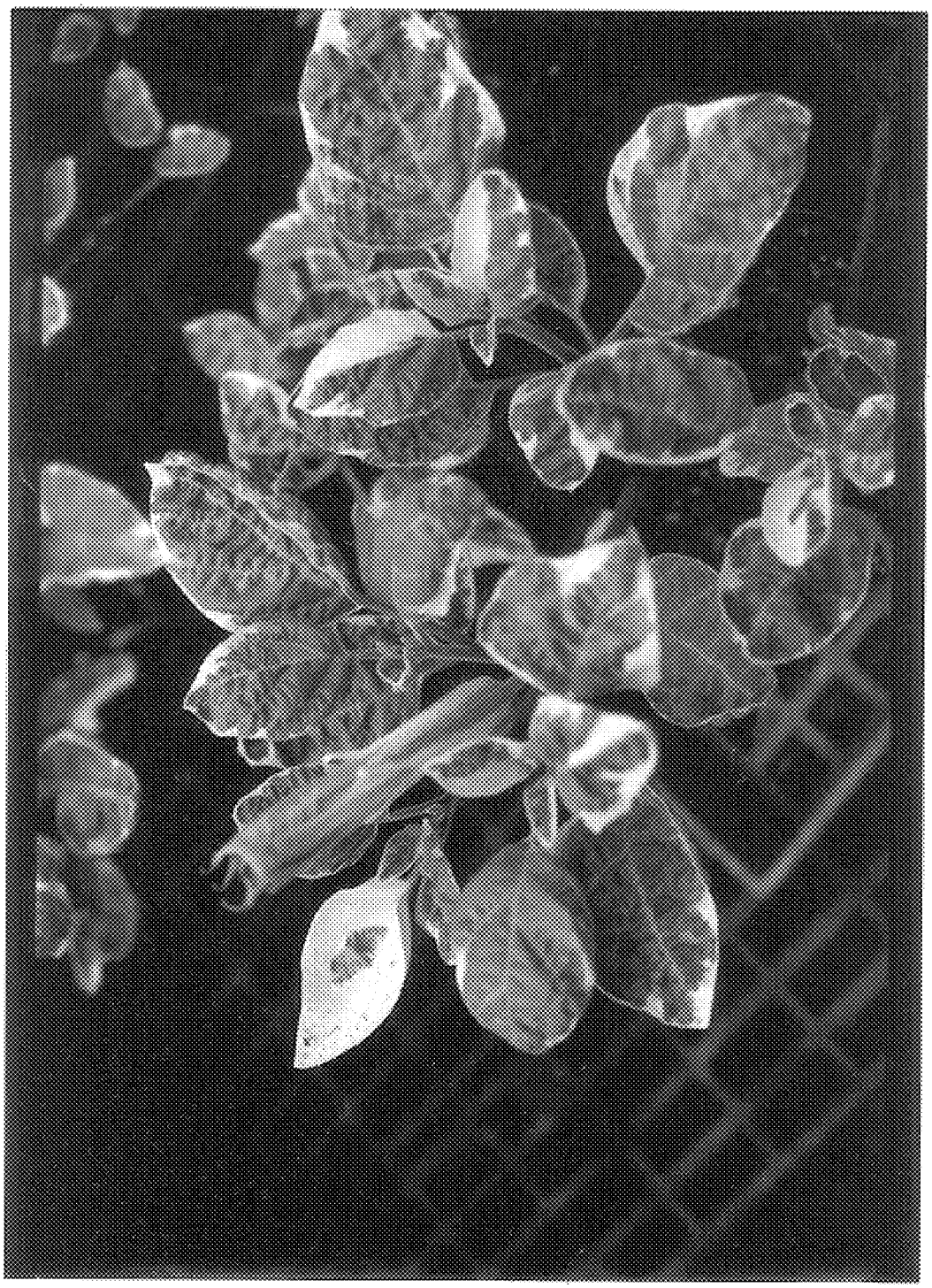
FIG. 2 Photograph of young plant with flower opening.
Figure 3:
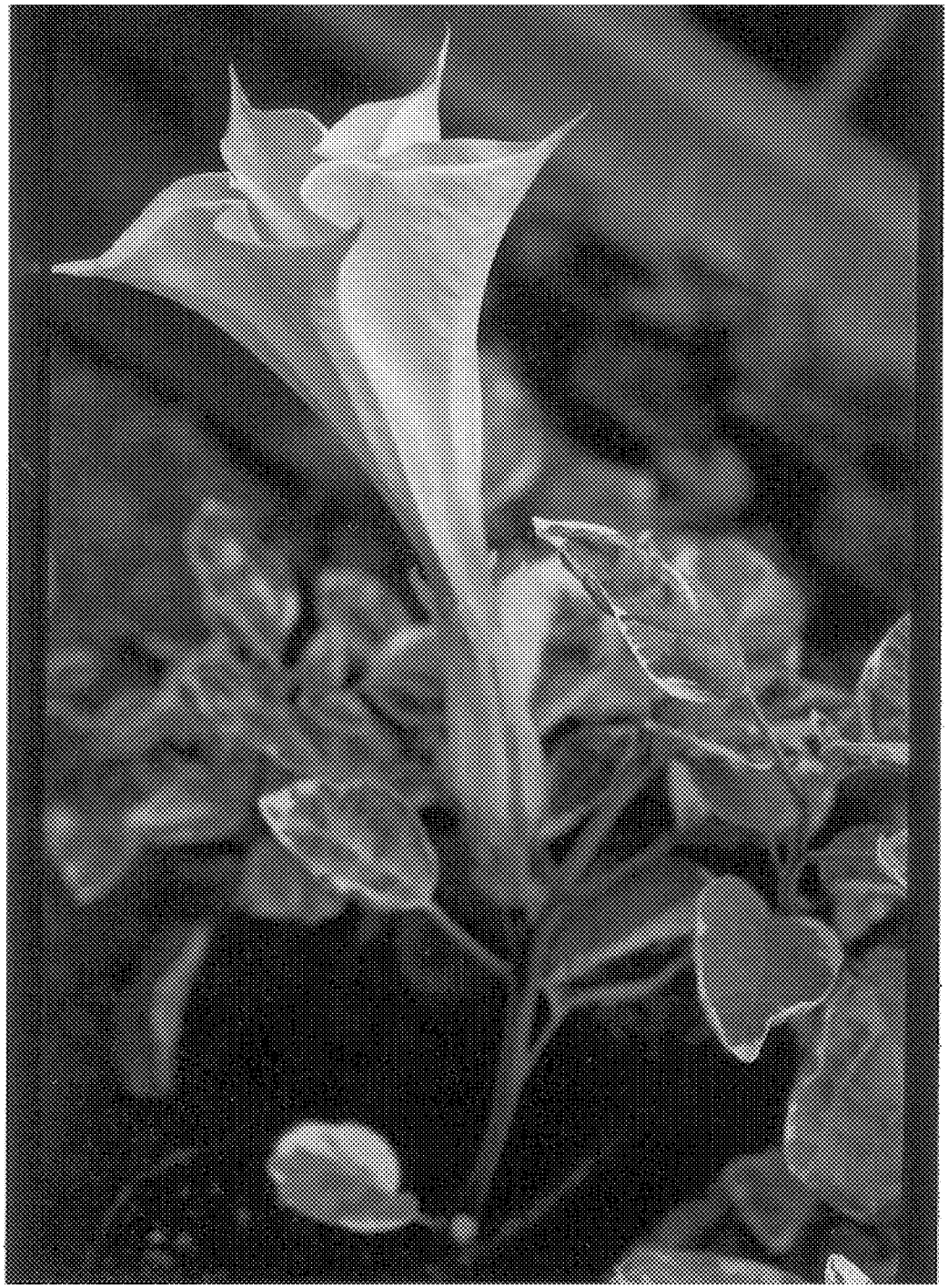
FIG. 3 Photograph of opening flower showing variegated calyx.
Figure 4:
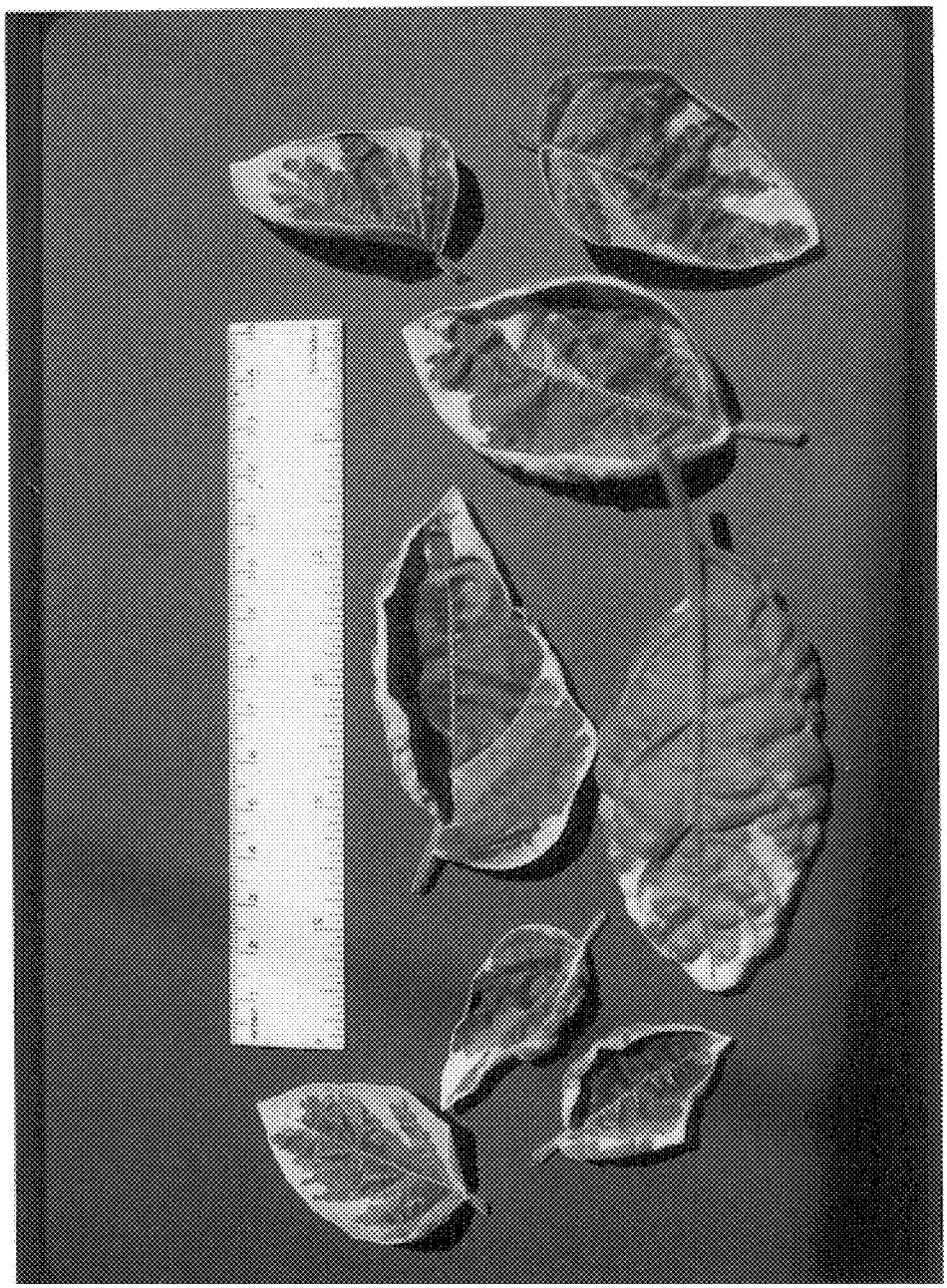
FIG. 4 Photograph of leaves of various ages.
Figure 5:
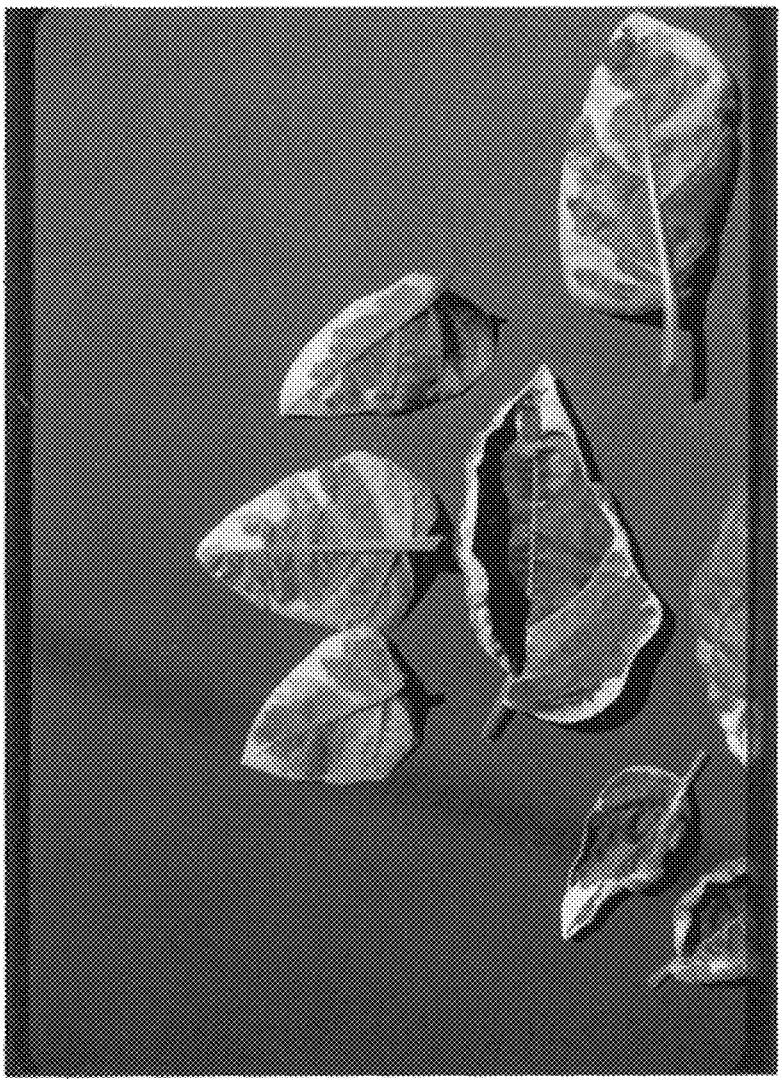
FIG. 5 Photograph of leaves showing purplish coloration of undersides of new growth.
Figure 6:
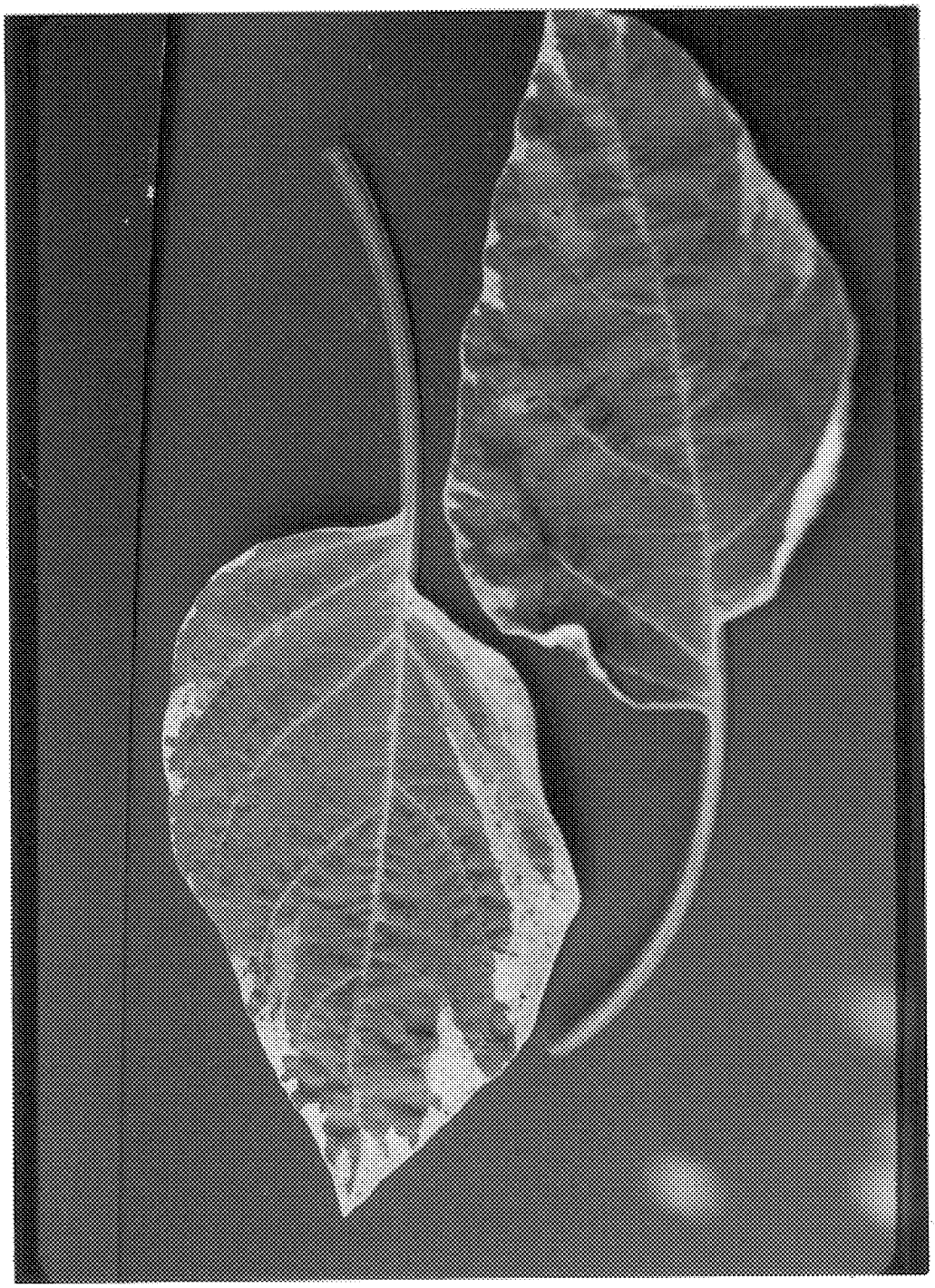
FIG. 6 Closeup photograph of mature leaves.
Figure 7:
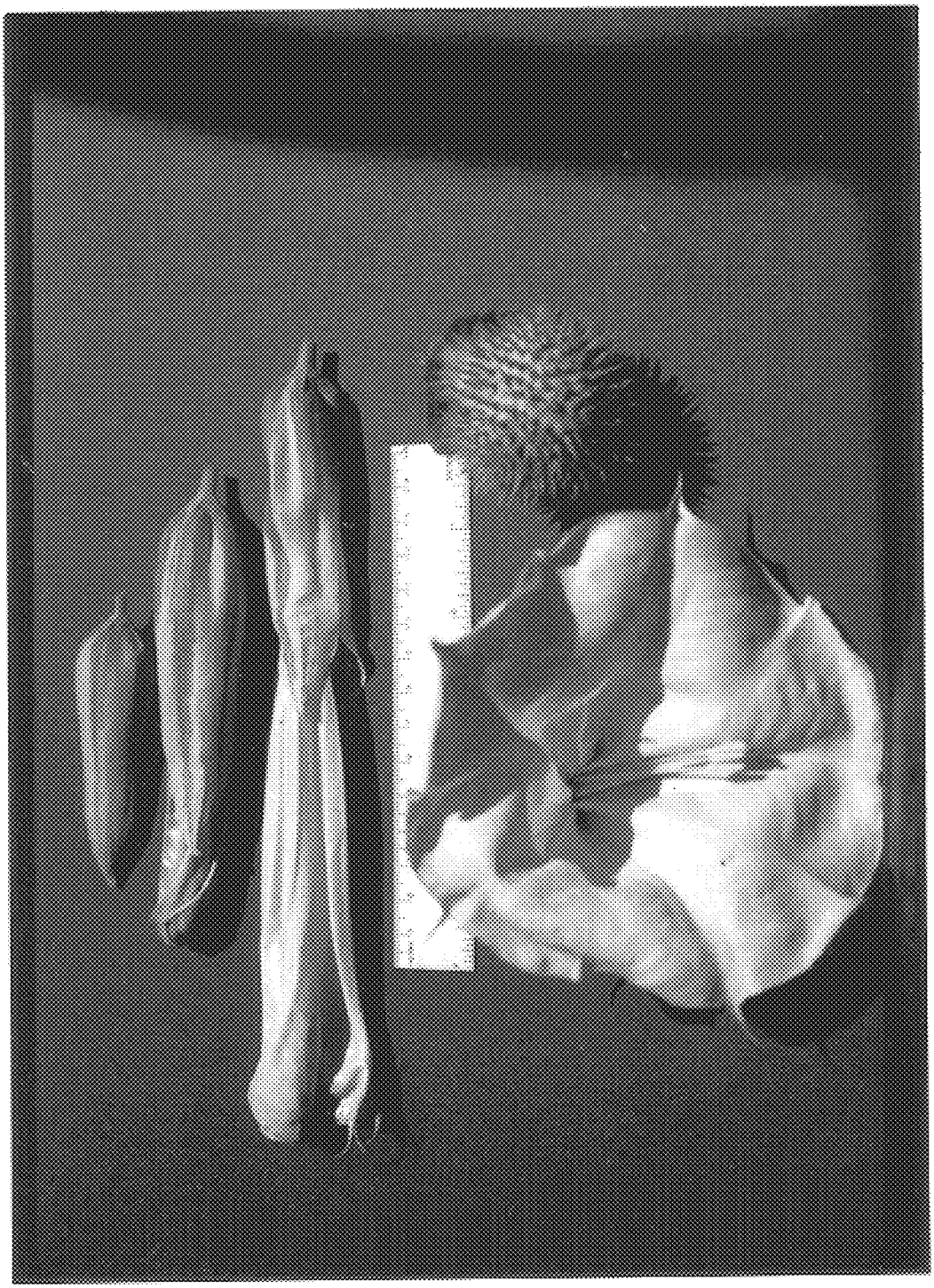
FIG. 7 Photograph of flower bud, opening buds, flower, and fruit.
Figure 8:
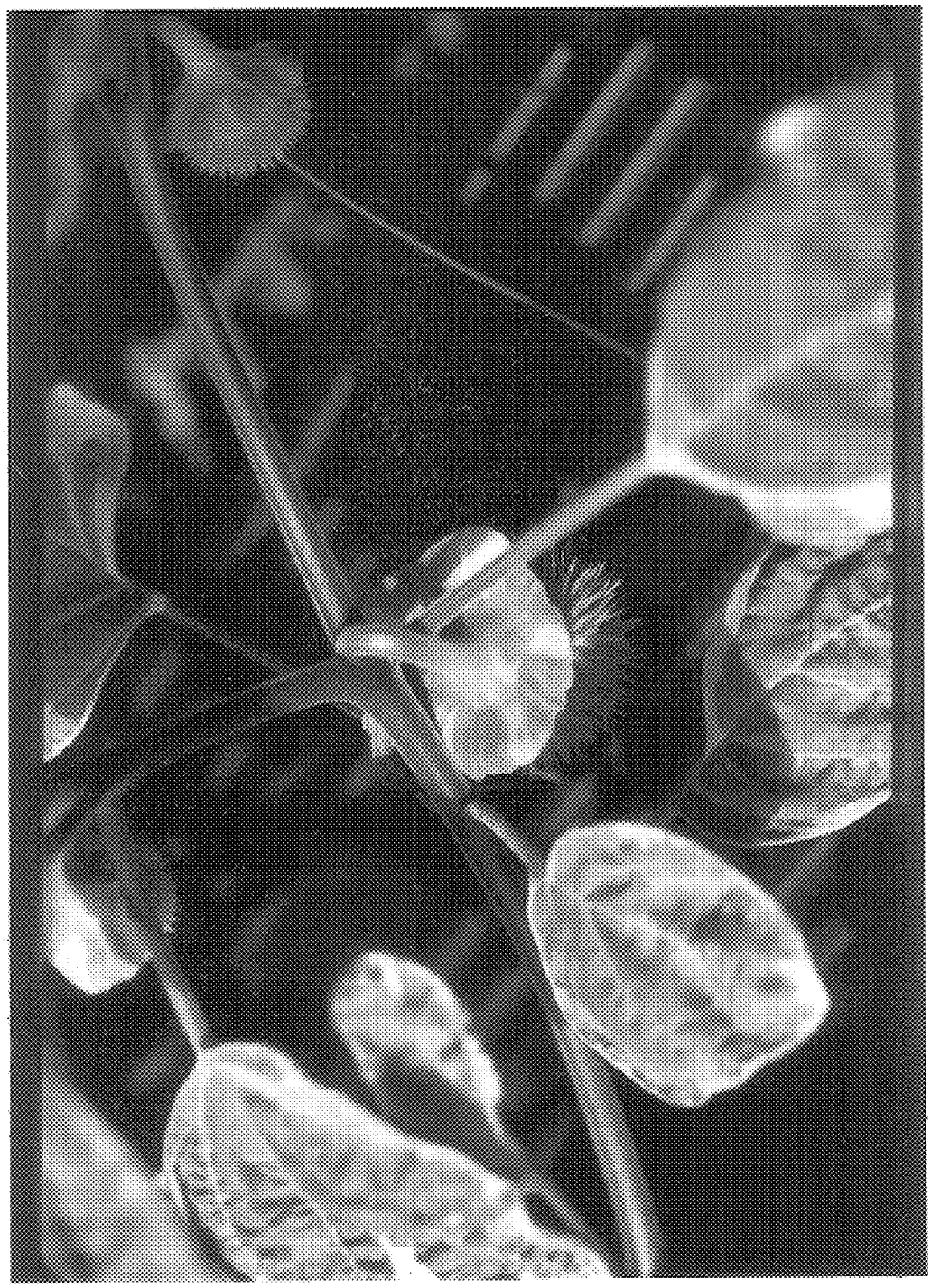
FIG. 8 Photograph of calyx base of fruit, and stems.
Figure 9:
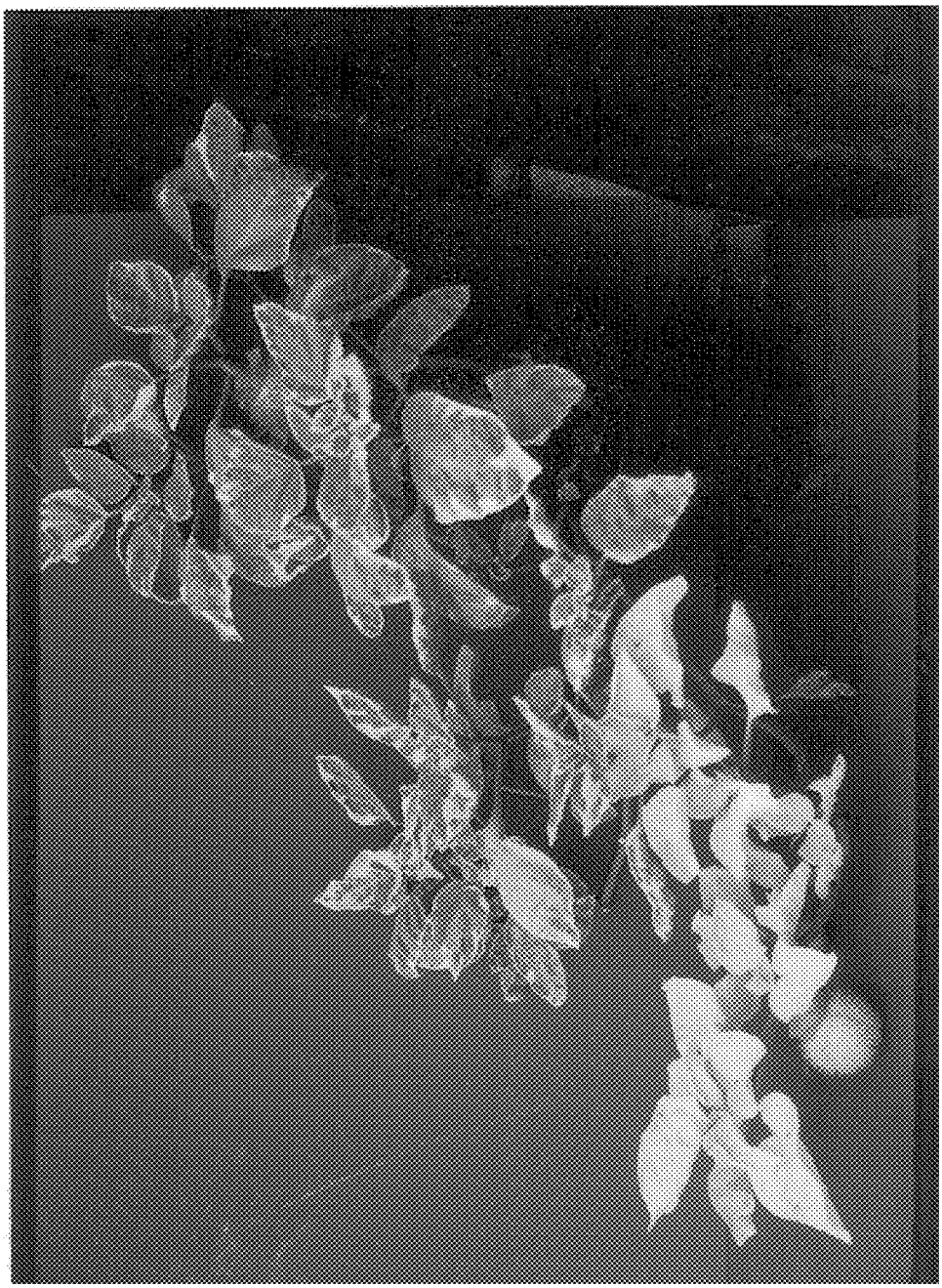
FIG. 9 Photograph of occasional light yellow shoot with light yellow fruit.

The following is a detailed description of my new cultivar, *Datura wrightii* 'Reverend Schusler', and the characteristics that distinguish the new Datura from its parent and other Daturas currently cultivated and sold in the floricultural trade. Descriptions are made from plants propagated from rooted cuttings of various ages(one to 12 months old), observed growing during the summer through winter of 1998 and spring and summer of 1999 in Corsicana, Tex. Plants were grown in containers and in the ground out-of-doors and also in containers in the greenhouse. (All color references are from The Royal Horticultural Society Colour Chart except where general terms of ordinary dictionary significance are used).

Foliage:

*Leaf shape and size.*—Leaves alternate, entire, irregularly ovate, with acuminate apices. Leaves have a puckered surface when young that lessens with maturity. The leaf margin is entire to slightly undulate or irregularly lobed, the margins upturned when young, flattening with age. Mature leaf blade 15 to 16 cm long down midrib, 10.5 to 11 cm wide at widest point. The upper and lower surfaces having microscopic hairs, particularly numerous along veins and blade margins. The lower hairs often observed with a small droplet on the end suggestive of a trichome. Petiole tomentose, 6.0 to 7.0 cm to first contact with blade, then another 1.5 to 2.0 cm to other side of blade, the leaf base being irregular with one side 1.5 to 2.0 cm lower than the other side.

*Leaf variegation and color.*—Young foliage marked by irregular patterns toward center of leaf, of grey green, 191A, with areas of a lighter grey green, 194B, the green area being broken by irregular variegation, greyed yellow, 160A along the margins proceeding in some areas all the way to the midrib, irregular splotches of dark green, 189A, over entire blade area. As leaves mature the variegated area fades to pale yellow, 11D, and becomes less prominent. Undersides of leaves have a purplish tint, 186A, that fades as leaves mature. This purplish coloration does not occur during the higher light and temperatures of summer. Instead the underside of the leaves is the same variegated and green color pattern as the above side, only paler. The tomentose petioles are a greyed-purple color, 186B. Occasionally a branch will be produced with the leaves and fruit entirely variegated, the new leaves opening a light yellow, 11C, fading to a very pale yellow, 8D, the entire surface having irregular blotches of dark green, 189A.

Flowers:

*Flower shape and size.*—The large flowers are single. The puffy, conical, upright flower buds are produced singly, in the axils of the forked branches from April to November. The corolla emerges from the calyx tube which is about 10 cm. long. The five sepals are fused but the upper end separates into 5 acute to acuminate lobes about 2 cm in length, 5 to 10 mm in width, and separated at the tips about 5 to 10 mm by a "V" shaped sinus. The corolla tube(5 fused petals) being about 20 cm. long. The corolla tube opens and flattens across the top to form a single, 5 lobed, funnelform to salverform flower, 12 to 15 cm. wide. The 5 lobes acuminate, about 1 to 2 cm. long. A ridge or fold composed of three prominent main veins runs from the base of the corolla tube to the base of the lobes. The five, 18 to 19 cm long, white filaments are attached to the corolla tube at the base but become separate 9 to 10 cm up, slightly protruding past the perianth. Each filament ends in a single somewhat flattened anther, 3 to 4 mm wide and 9 to 10 mm long, an off-white to tan in color. The single, white, round style is about 1 mm wide and 19 to 20 cm in length and protrudes past the perianth and stamens. The stigma is somewhat rounded, with flattened sides, 1 to 2 mm in width. The single yellow-green ovary is approximately 5 to 7 mm long and 5 to 7 mm wide, with small hairlide protrusions that will later become the spines on the fruit. Mature plants have been observed with more than 20 flowers open at the same time. Individual flowers being attractive for 2 to 3 days. Flowers have a sweet fragrance and are very attractive to bees.

*Flower color.*—Calyx buds (in cooler weather) are a greyed-purple, 186D, with 5 streaks or bands of grey-green, 194B. Both become lighter as they mature. During high light and temperatures of late summer the purple coloration is faint and the calyx tube is more white but the 5 bands of grey-green, 194 B remain true. The corolla tube before opening is mainly a yellow-white, 158B, with streaks of green-white, 157A, radiating from the base, with the tips being greyed-purple, 186D. As it opens the corolla edges are a light red-purple, 69D, fading to white, the corolla edges curling backwards as the flower matures. During the high light and heat of summer the corolla tube before opening is a yellow-white, 158B with streaks of green-white, 157A radiating from the base.

Fruit:

*Fruit shape and size.*—Fruit a globose, stipitate capsule covered with numerous spines. The capsule is attached to the branch axils by the 2 to 3 cm pedicel that arches downwards, causing the fruits to appear pendulous, similar to Christmas ornaments hanging on a Christmas tree. Pericarp about 4 to 5 cm. wide and about 4 cm. from base to tip. Spines about 0.5 cm. long. The base of the calyx forming an undulate collar at the base of the fruit, about 4 to 5 cm. wide across bottom and drooping down about 1 to 1.5 cm. all around base of pericarp. Fruit irregularly dehiscent, two chambers, each fruit containing 50 to 100, crescent-shaped, light tan seeds about 5 mm. in length.

*Fruit color.*—Pericarp and spines a grey-green, 193D, with a band or spot of yellow, 4C, at the top of the pericarp near the point where the style attached. Calyx base a grey-green, 191B, with bands of yellow green, 147D and yellow, 4D. Fruits become dry and turn red-brown to light tan at maturity.

Stems:

*Stem branch habit.*—The plant has an irregular shape, the stems branching into twos. The overall habit being semi-upright to procumbent, plants being 0.33 to 1 meter in height to 1 meter wide.

*Stem color.*—Stems finely tomentose, greyed-purple, 186B to 187A.

Hardiness: Plants observed at Corsicana, Tex. (U.S.D.A. hardiness zone 7B) grow as herbaceous perennials that die back to the ground around November. Plants in the ground during the winter of 1998–1999 continued growth from the stumps in April of 1999 and grew abundantly until die back in November. However, I would not consider this plant to be reliably cold hardy and would classify it as a frost tender perennial. Plants grown in containers in the greenhouse have continued to grow for 3 years.

Resistance to pests: No particular disease or pest resistance has been observed although plants were basically unaffected by large populations of grasshoppers over several years.

Propagation: The unique variegation pattern of this plant is retained by propagation through the use of stem cuttings, treated with a rooting hormone, and placed under a mist system. Cuttings root in 3 to 4 weeks time.

Plant vigor: Plants thrive on sun and high temperatures and grow vigorously. Plants about 15 cm tall and 20 cm wide when planted into the ground in May can reach 75 cm tall and 1 meter wide by October. Plants are somewhat drought tolerant. Plants have survived periods of wilting with no apparent long-term affects.

Distinguishing features: The yellow, white, and green shades of color and pattern of the variegated foliage, calyx, and fruit distinguishes this plant from the parent and other Daturas that have leaves that are all green to gray green, green calyx tube, and green fruit. The inventor knows of no other variegated *Datura wrightii* cultivars. The variegation increases the aesthetic value of this plant as a container plant or ornamental bedding plant.

I claim:

1. A new and distinct cultivar of Datura plant named 'Reverend Schusler', as illustrated and described, characterized by having variegated foliage, variegated calyxes, and variegated fruit.

* * * * *